United States Patent [19]

Bull

[11] 4,302,976
[45] Dec. 1, 1981

[54] WHEEL PROBES

[75] Inventor: Reginald B. Bull, Thatcham, England

[73] Assignee: British Gas Corporation, London, England

[21] Appl. No.: 85,701

[22] Filed: Oct. 17, 1979

[30] Foreign Application Priority Data

Jul. 19, 1979 [GB] United Kingdom ............... 25199/79

[51] Int. Cl.³ ............................................. G01N 29/04
[52] U.S. Cl. ..................................................... 73/639
[58] Field of Search ................. 73/639, 638, 637, 640, 73/635

[56] References Cited

U.S. PATENT DOCUMENTS

| | | | |
|---|---|---|---|
| 2,545,101 | 3/1951 | Meunier | 73/639 |
| 3,205,702 | 9/1965 | Joy | 73/639 |
| 4,055,990 | 11/1977 | Topping | 73/638 |
| 4,174,636 | 11/1979 | Pagano | 73/639 |
| 4,202,216 | 5/1980 | Bull et al. | 73/639 |
| 4,217,782 | 8/1980 | Punt | 73/639 |

*Primary Examiner*—Anthony V. Ciarlante
*Attorney, Agent, or Firm*—Watson, Cole, Grindle & Watson

[57] ABSTRACT

A wheel probe for ultrasonically inspecting a component, such as the wall of a pipe, is of hollow form to define a chamber in which at least one ultrasonic transducer is supported to direct and receive ultra-sound through the wheel probe. The chamber is filled with an acoustic coupling liquid, and at least one resilient diaphragm is provided in the wall of the chamber so as to deflect in response to a difference in pressure thereon and balance the pressure of the liquid with that of the environment about the wheel probe.

9 Claims, 9 Drawing Figures

WHEEL PROBES

BACKGROUND OF THE INVENTION

1. Field of the Invention

This invention relates to wheel probes used for ultrasonically inspecting a component, and in particular to wheel probes used in ultrasonic pipe inspection apparatus that can be inserted into the bores of pipes so as to examine the walls of the pipes for defects, cracks or other discontinuities.

2. The Prior Art

The usual pipe inspection apparatus for examining, for example, gas pipelines, comprises a vehicle or a train of vehicles which are propelled along the pipeline by the gas flow in the pipeline. In one arrangement, ultrasonic transducers are mounted in a number of wheels (usually referred to as "wheel probes") which are urged into contact with the wall of the pipe. In use, ultrasound generated by the transducers is transmitted across the interface between the wheel probe and the wall of the pipe into the pipe wall. Ultrasound reflected or refracted from within the pipe wall is in turn received by the transducers within the wheels and subsequently analyzed.

In co-pending U.S. Pat. Application Ser. No. 933,031, filed Aug. 11, 1978, now abandoned there is described a wheel probe for insertion into the bore of a pipe for the purpose of ultrasonically inspecting the wall of the pipe. The wheel probe comprises a solid annular rim made of a non-deformable material (through which sound will pass) and side members, the side members and the rim defining a hollow chamber in which is contained a liquid acoustic coupling medium through which ultrasound will pass. One or more ulrasonic transducers are located within the chamber and are positioned adjacent the inside surface of the rim for directing and receiving sound through the rim, as well as a solid, resilient tire member mounted on the outside surface of the rim.

However, it has been found that in the highly pressurized gas environment of a gas pipeline, the seals used in the probe wheels for maintaining the probe wheel chamber fluid tight have failed, with consequent loss of the liquid acoustic coupling medium and the formation of large bubbles in the liquid which interfers with the passage of ultrasound. Furthermore, the wheel construction must have sufficient strength to withstand the pressure; this not only increases the weight of the probe, but also reduces the passage of ultrasound due to increased thickness of the probe wheel rim.

An object of the present invention is to provide an improved wheel probe designed to remedy the aforesaid disadvantages and limitations of known wheel probes.

SUMMARY OF THE INVENTION

According to the present invention, there is provided a wheel probe for ultrasonically inspecting a component which comprises a wheel of hollow form so as to provide therein a chamber adapted to be filled with an acoustic coupling liquid, at least one ultrasonic transducer supported within the chamber so as to direct and receive sound through the rim of the wheel, and at least one obturator adapted to be exposed on one side thereof to the liquid and on the other side thereof to an ambient environment about the wheel probe, the obturator being resiliently movable in a direction towards and away from the environment so as to move in response to a difference in pressure thereon and balance the pressure of the liquid with that of the environment.

The obturator may be at the side of the wheel or situated at a compartment adapted to be connected by duct means to the chamber, and a plurality of wheel probes may share a common compartment.

Desirably, means are provided for biasing the obturator in a direction towards the environment.

In one arrangement according to the invention the transducer may be supported by a mounting member around which the wheel is rotatable, and the mounting member may define at least in part the duct means.

Preferably, the obturator comprises a resilient diaphragm.

The invention will now be further understood by reference to the accompanying drawing taken in conjunction with the following discussion:

DETAILED DESCRIPTION OF THE PREFERRED EMBODIMENTS

Figure 1:
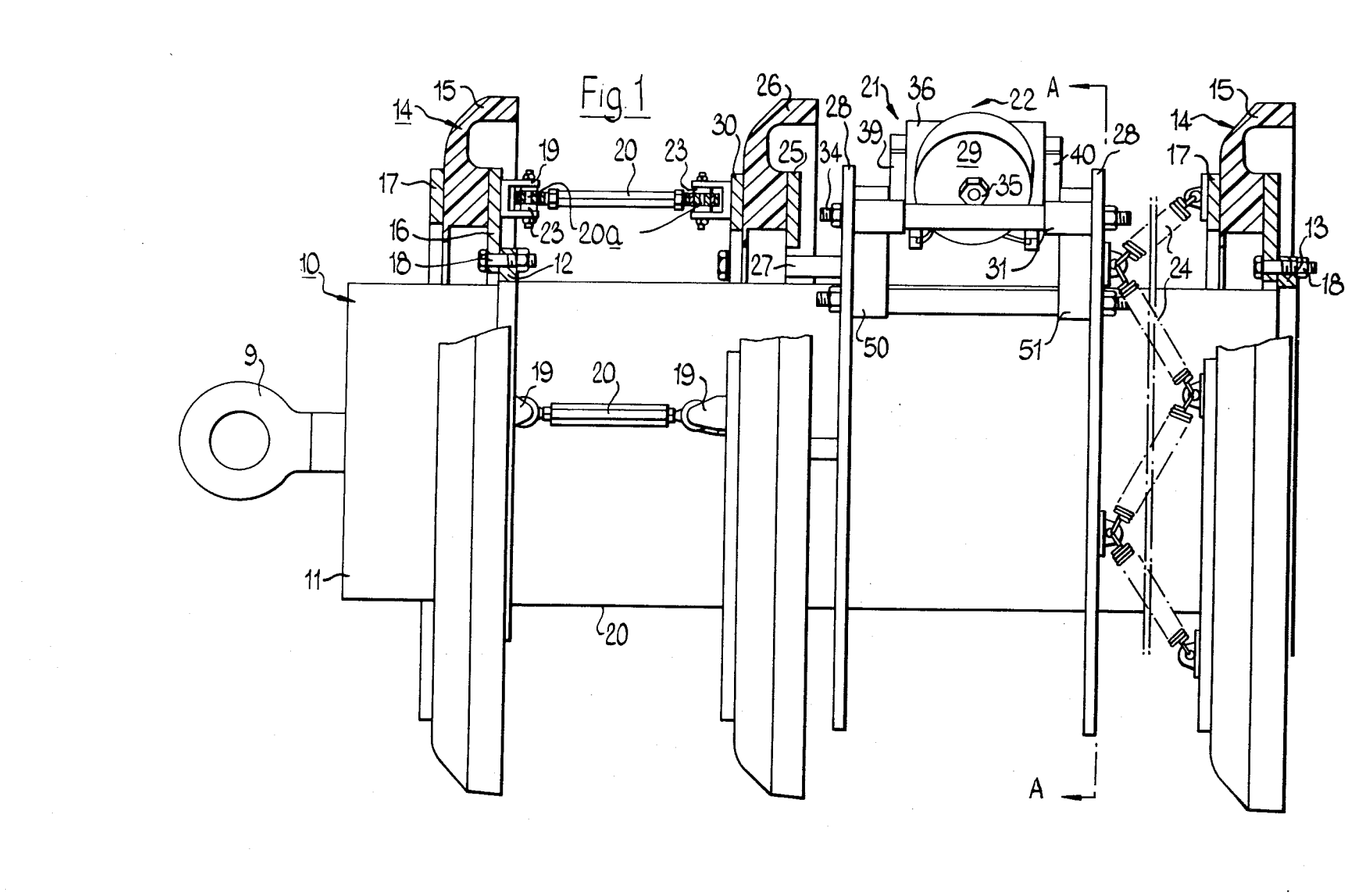
FIG. 1 shows a part sectional side elevation of an apparatus for ultrasonically inspecting the wall of a pipe.

In the Figures, like parts have like numerals. Referring first to FIG. 1, the apparatus shown is intended for insertion in a gas pipe line (not shown) and comprises a vehicle 10 provided with a towing eye 9 that enables the vehicle 10 to be towed by a second vehicle (not shown) which is propelled along the pipeline by the flow of of pressurized gas in the pipe. The vehicle is the subject of co-pending U.S. Patent Application Ser. No. 067,790, filed Aug. 20, 1979.

The vehicle 10 comprises a central hollow tubular member 11 having two flanges 12, 13 located at or near respective ends of the vehicle, and alignment means 14 mounted on each flange for the purpose of locating and aligning the vehicle 10 along the axis of the pipe. Each alignment means 14 comprises an annular sealing member 15 made of an elastomeric material such as polyurethane, and each has a concave recess facing towards the rear of the vehicle 10 to assure that each sealing member 15 will be urged into engagement with the bore of the pipe by the pressurized gas in the pipe. The annular sealing member 15 is clamped between an annular plate 16 and a clamping plate 17, the annular plates 16 being secured by bolts 18 to the respective flanges 12, 13.

A number of brackets 19 (only two are shown) equispaced around a common pitch circle are secured to the front annular plate 16, and a link 20 is mounted by a spherical ball joint 20a at one end to pivot 23 in each bracket 19. A spherical ball joint 20a in the free end of each of the links 20 locates about a pivot 23 in a respective bracket 19 secured to an annular support plate 30, the brackets 19 being arranged so that the pivots 23 lie approximately radially relative to the front annular plate 16.

The support plate 30 forms part of a carrier 21 having two annular carrier plates 28 spaced apart in parallel relationship by hollow spacers 31 and secured together by bolts 34 extending through the spacers 31, the bolted together carrier plates 28 being fixed to the support plate 30 by bolts 27. The carrier 21 is freely movable in a plane normal to the longitudinal axis of the vehicle 10, and is suspended on springs 24 attached to the annular plate 17 of the rearmost alignment means 14 and to the rearmost carrier plate 28. The carrier 21 has a rubber centralizing support plate 30 to centralize the carrier 21 in the bore of the pipe. Eight inspection devices 22 (only one is shown) are resiliently supported between the carrier plates 28, each inspection device 22 having two wheel probes 29 (only one is shown), a wheel probe 29 being shown in greater detail in FIGS. 3 to 4a to which reference is now made.

Figure 3:
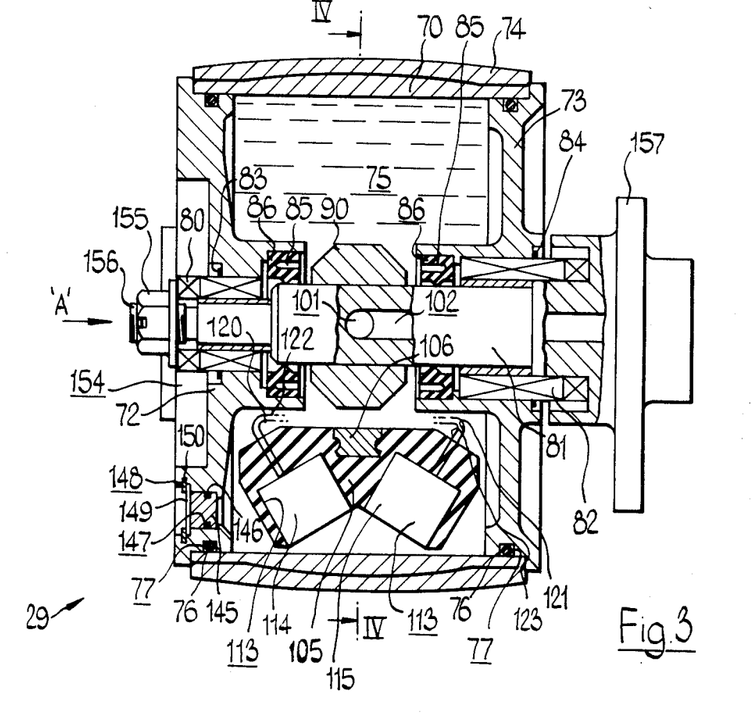
FIG. 3 is a fragmentary sectional view on the line III—III of FIG. 2.
Figure 4:
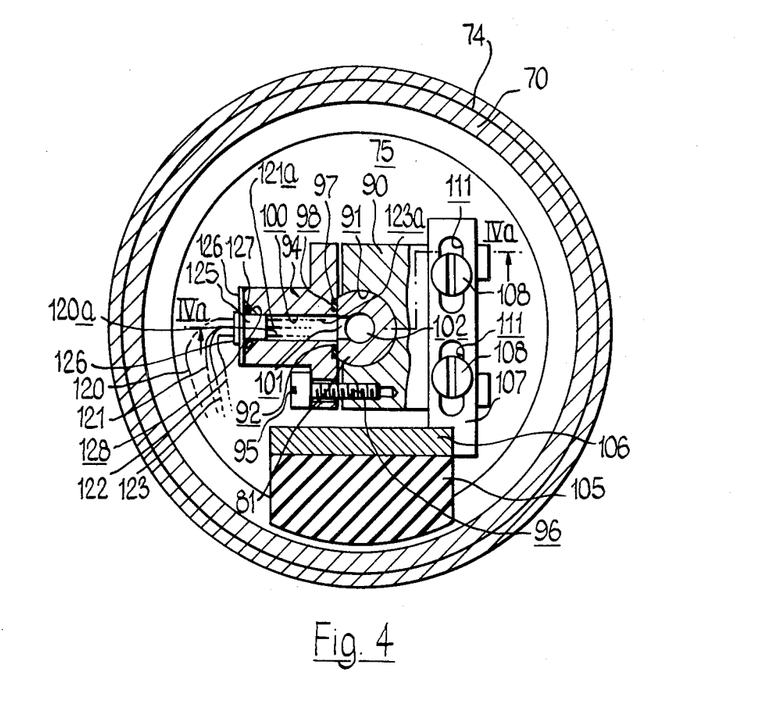
FIG. 4 is a sectional view on the line IV—IV of FIG. 3.
Figure 4A:
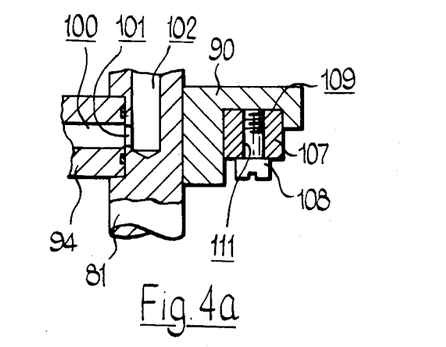
FIG. 4a is a fragmentary sectional view on the line IVa—IVa of FIG. 4.

The wheel probe 29 shown comprises a hermetically sealed hollow body having a Nylon (Type 12) rim 70 with a solid polyurethane tire 74 thereon and left hand and right hand brass side plates 72, 73, respectively, which define therebetween a chamber 75, an 'O' ring seal 76 being provided in a circumferential groove 77 in each side plate 72, 73. The left hand side plate 72 is mounted on a combined needle journal and ball thrust bearing 80, which is itself mounted on a steel stepped shaft 81 which extends through the right hand side plate 73 and provides a mounting for a combined needle journal and ball thrust bearing 82 which rotatably supports the right hand side plate 73, the bearings 80, 82 being retained by respective circlips 83, 84. GACO radial oil seals 85 located one in a respective circular recess 86 in each side plate 72, 73 bear circumferentially around the stepped shaft 81.

A brass mounting block 90 has a part circular bore 91 through which the stepped shaft 81 extends, the stepped shaft 81 having a local flat portion 92 extending slightly above the corresponding surface of the mounting block 90. A nylon clamp block 94 is held against the flat portion 92 by screws 95 (only one is shown) which engage in corresponding threaded recesses 96 in the mounting block 90, an 'O' ring seal 97 in an annular recess 98 in the clamp block 94 providing a seal between the clamp block 94 and the flat portion 92. A hole 100 extends centrally through the clamp block 94 and is aligned with a corresponding hole 101 in the stepped shaft 81 and which leads to an axial hole 102 that extends to the right hand end of the stepped shaft 81.

A probe support block 105 of silicone rubber has a moulded insitu metal arm 106, the arm 106 having perpendicular thereto a slider member 107 which locates in a slide 109 in the mounting block 90 and is secured to the mounting block 90 by screws 108 which locate through corresponding slots 111 in the slider member 107 to allow adjustment of the position of the probe support block 105 towards and away from the rim 70. The probe support block 105 at that portion thereof adjacent to the rim 70 is 'V' shaped and has two opposing cylindrical recesses 113 in which are located respective ultrasonic transducers 114, 115 to transmit a sonic signal reflected by the pipe. A respective power line 120, 121 for energizing the transducers 114, 115 and a respective signal line 122, 123 from the transducers 114, 115 extend from respective transducers 114, 115 to a terminal member 125 having a flange 126 secured by screws (not shown) to the clamp block 94 and which sealingly traps an 'O' ring seal 127 in a frusto-conical recess 128 in the clamp block 94. Corresponding power lines 120a, 121a, and signal lines 122a, 123a extend from the terminal member 125 through the hole 100 in the clamp block 94 and the holes 101 and 102 in the stepped shaft 81, and are fed by way of leads (not shown) to the towing vehicle or to a further vehicle (not shown) which is towed behind the vehicle 10.

Figure 5:
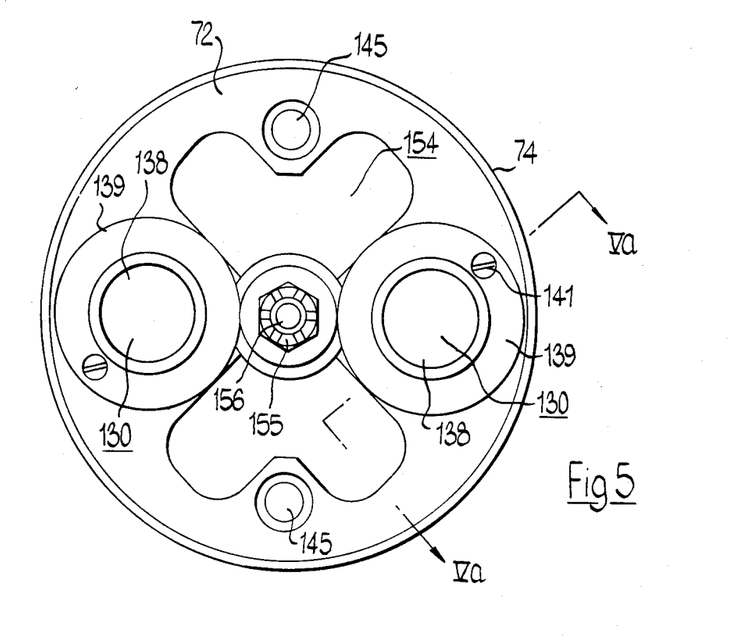
FIG. 5 is a view in the direction of arrow 'A' of FIG. 3.
Figure 5A:
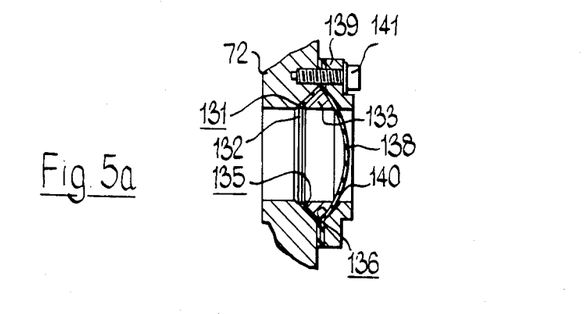
FIG. 5a is a fragmentary sectional view on the line Va—Va of FIG. 5.

Referring now to FIGS. 5 and 5a, the left hand side plate 72 has two diametrically disposed apertures 130 each having a frusto-conical seating 131 in which a Neoprene synthetic rubber annular seal member 132 is held by a form ring 133 having opposing frusto-conical end faces 135, 136. An obturator in the form of a Neoprene synthetic rubber diaphragm 138 is held against each form ring 133 by a clamp ring 139 having a frusto-conical seating 140 corresponding with the shape of the form ring 133 so as to bias the respective diaphragm 138 outwardly towards the environment, four screws 141 (only one is shown) clamping each assembly of seal member 132, form ring 133, diaphragm 138 and clamp ring 139 to the left hand side plate 72.

Figure 2:
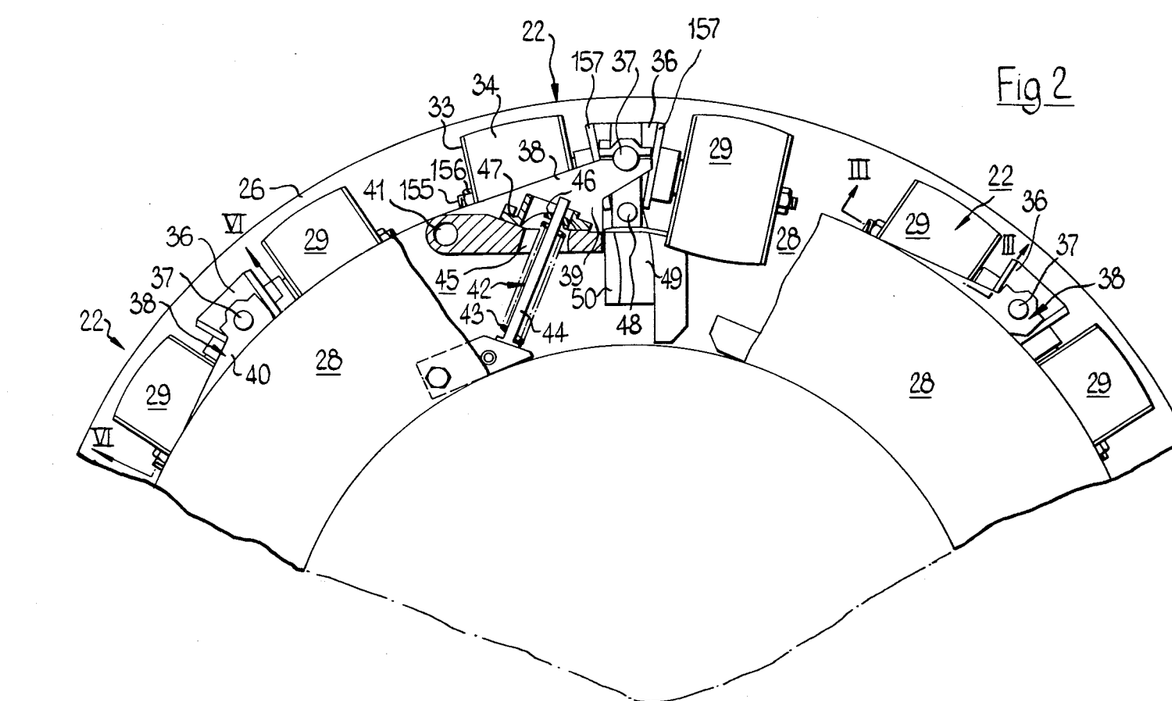
FIG. 2 is a fragmentary, partly broken away end view of the apparatus of FIG. 1 looking in the direction of arrows A.

Referring again to FIG. 3, two plug members 145 (only one is shown in FIG. 3) each have an 'O' ring seal 146 in a circumferential groove 147 located in a respective stepped aperture 148 in the left hand side plate 72 and have a shoulder 149 which is retained by a circlip 150 after the chamber 75 has been filled under vacuum conditions with an acoustic coupling liquid (not shown) such as for example a mixture of glycerol and water, and which in some instances may be loaded with particles of graphite, or molybdenum disulphide. The left hand side plate 72 is relieved locally at 154 to reduce the weight of the wheel probe 29 and both the side plates 72, 73 are clamped to the rim 70 by a nut 153 on a threaded end 156 of the stepped shaft 81, the other end of the stepped shaft 81 having a flange 157 which is clamped as shown in FIG. 2 to a taper block 36 (not shown in FIG. 3) which is itself pivotally mounted on a spindle 37 carried at the free end of the limbs of a generally "U" shaped pivot about the axis of the spindle 37 so that the two wheel probes 29 of each inspection device 22 contact the bore of the pipe along lines which are equi-spaced on each side of a radial plane passing through the longitudinal axis of the pipe and the longitudinal axis of the spindle 37. The spindles 35 lie normal to radial planes passing through the point of contact between the wheel and the bore of the pipe.

The pivot arm 38 comprises two spaced side members 39, 40 connected by a shaft 41 about which the pivot arm 38 rotates. The pivot arm 38 is mounted between the carrier plates 28, and a spring assembly 42 operates on each side member 39, 40 to urge the wheel probes 29 radially outwards into engagement with the bore of the pipe. Each spring assembly 42 comprises a compression coil spring 43 mounted on a rod 44 which is rigidly mounted at one end on the carrier plate 28. The coil spring 43 passes through an elongate slot 45 in the pivot arm 38, and urges a thrust pad 46 into engagement with a concave surface of a bracket 47 secured to the pivot arm 38.

Each taper block 36 is provided with spigots 48 which engage in guideways 49 provided in end stops 50 carried by the carrier plates 28. The guideways 49 are shaped to provide a limit to the pivotal movement of taper block 36 while allowing some pivotal movement of taper block 36 when the wheel probes 29 are negotiating irregularities in the pipe surface such as ovality or welds, and may also assist in maintaining the wheel probes 29 correctly aligned relative to the pipe wall so that the wheel probes 29 contact the pipe wall along lines equi-spaced about radial planes.

In use, i.e., when the vehicle 10 travels along the bore of a pipe containing a pressurized gas so that the wheel probes 29 engage and run along the wall of the pipe, the pressure of the gas on the diaphragms 138 produces a corresponding pressure on the acoustic coupling liquid in the chamber 75 as the diaphragms 138 deflect so that the pressures inside and outside the wheel probes 29 are automatically brought into balance, and any residual air bubbles in the acoustic coupling liquid are reduced as a result of the increased pressure of the acoustic coupling liquid.

The diaphragms 138 also provide a safety feature in the event of any pressurized gas leaking into the chamber 75, since on the removal of the wheel probe 29 from the pressurized gas pipe into atmospheric conditions, any gas in the chamber 75 can expand against the deflection of the diaphragms 138 so as to relieve the pressure inside the wheel probe 29. In this respect the diaphragms 138 also act as visual indicators of the presence of pressurized gas in the chamber 75 from the extent of the deflection produced by entrapped pressurized gas. Furthermore, the diaphragms 138 allow volume changes of the wheel probe 29 and of the acoustic coupling medium to take place when the wheel probe 29 is used in pipelines of differing temperatures.

It is to be understood that the number of diaphragms 138 used in a wheel probe 29 may be selected to suit particular applications depending on the temperature and pressure of the environments in which the wheel probe 29 is intended to be used.

Figure 6:
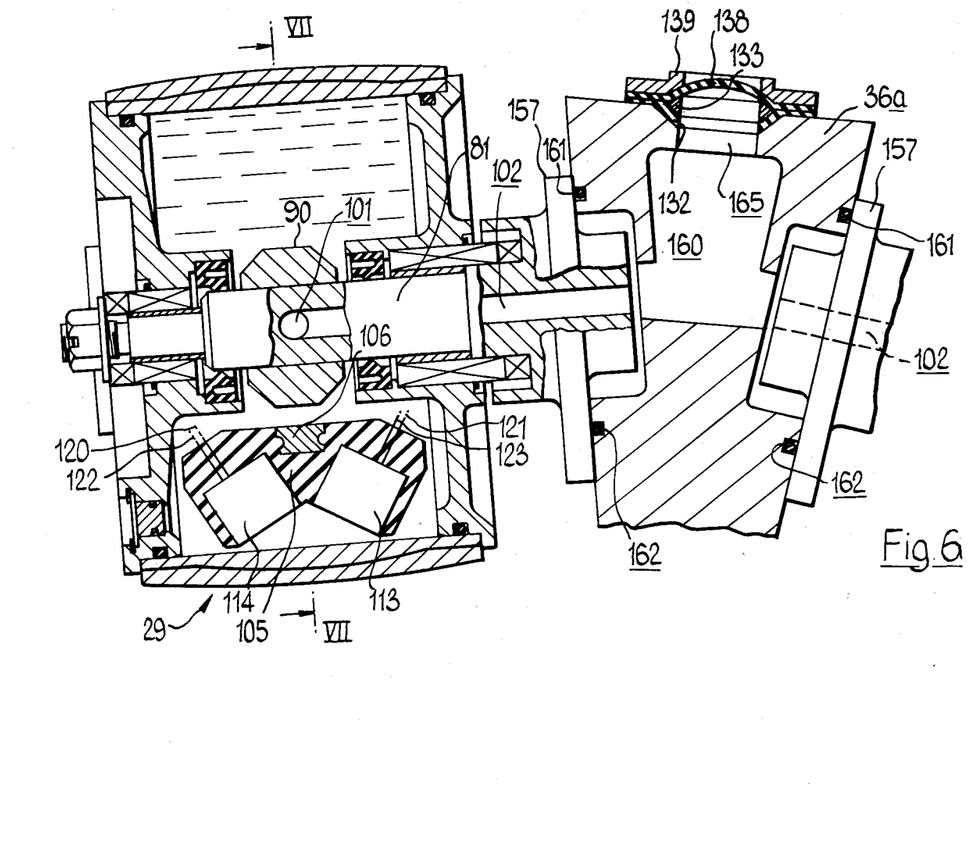
FIG. 6 is a fragmentary sectional view on the line VI—VI of FIG. 2.
Figure 7:
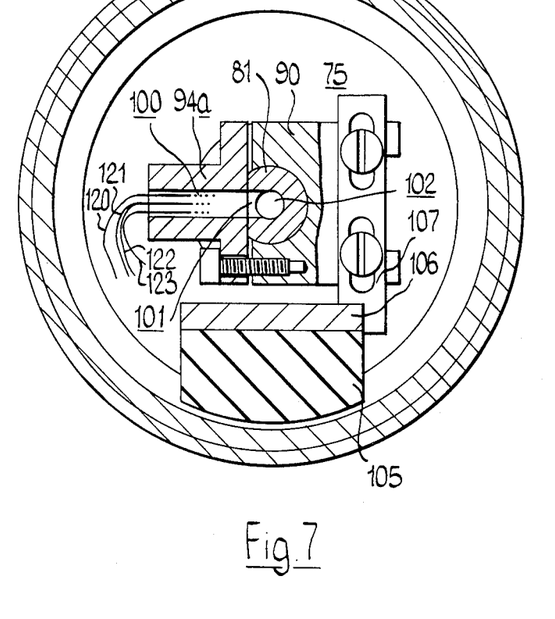
FIG. 7 shows a sectional view on the line VII—VII of FIG. 6.

An alternative to the incorporation of the diaphragm 138 in a wheel probe 29, the diaphragm 138 may be displaced from the wheel probe 29 as shown in FIGS. 6 and 7 to which reference is made.

The wheel probe shown in FIGS. 6 and 7 is similar in many respects to the wheel probe 29 shown in FIGS. 3 and 4, but the terminal member 125 of FIG. 4 has been dispensed with so that the power lines 120, 121, and the signal lines 122, 123, are extended to replace the power lines 120a, 121a and the signal lines 122a, 123a and extend through a modified clamp block 94a and the stepped shaft 81. The 'O' ring seals 97 and 126 in the clamp block 94 of FIG. 4 are no longer necessary since the acoustic coupling liquid is allowed to flow through the holes 101, 102 in the stepped shaft 81 to a chamber 160 in a modified taper block 36a to which is secured the flange 157 of each wheel probe 29, the flanges 157 each having an 'O' ring seal 161 in an annular groove 162. The chamber 160 has a port 165 closed by a diaphragm 138 held in a similar manner against the taper block 36a to that shown in FIG. 5a to which reference should be made for further details.

In use, deflection of the diaphragm 138 of FIG. 6 provides the self-adjusting feature of balancing the pressure of the acoustic coupling liquid in each of the wheel probes 29 with that of the surrounding environment.

It will be appreciated that alternative obturators may be used in accordance with the invention. It is also to be understood that alternative specific designs of transducers and the positions thereof inside the wheel probes may be used, for example, as described in co-pending U.S. Patent Application Ser. No. 67,791, filed Aug. 20, 1979 and 67,790, filed Aug. 20, 1979.

Furthermore, the number of brackets 19 and the inspection devices 22 may be selected to suit a particular diameter of gas pipeline in which the apparatus is to be used.

I claim:

1. A wheel probe for ultrasonically inspecting a component, said wheel probe being sealingly mountable around a central support means and rotatable with respect thereto, said wheel probe comprising
   a solid annular rim composed of a non-deformable material through which sound will pass,
   side members sealingly extendable between said solid annular rim and the central support means so as to define a hollow chamber which is filled with acoustic coupling liquid,
   at least one ultrasonic transducer mounted in said hollow chamber which is capable of sending and receiving sound through said annular rim,
   a solid, resilient tire member mounted on the annular rim on the side thereof opposite said hollow chamber, and
   at least one side member including at least one obturator which is exposed on one side to the ambient environment in which the wheel probe is located and on its opposite side to the liquid in said hollow chamber, each obturator being movable in response to the pressure differences on its opposite sides to balance the pressure of the acoustic coupling liquid in said hollow chamber with the pressure of the ambient environment.

2. The wheel probe of claim 1 including means for biasing each obturator in the direction of said ambient environment.

3. The wheel probe of claim 1 wherein each obturator comprises a resilient diaphragm positioned over a respective aperture in side wall to which it is attached.

4. The wheel probe of claim 1 wherein said solid, resilient tire member is composed of polyurethane.

5. An inspection device for ultrasonically inspecting a component, said inspection device comprising
   a wheel probe support means, said wheel probe support means including a duct means therein and mounting at least one obturator which is exposed on one side to the ambient environment in which the wheel probe support means is located and on its opposite side to said duct means, and
   at least one wheel probe rotatably mounted on said wheel probe support means, each wheel probe comprising a solid annular rim composed of a non-deformable material through which sound will pass, side members sealingly extending between said solid annular rim and the wheel probe support means so as to form a hollow chamber which is in fluid communication with said duct means in said wheel probe support means, at least one ultrasonic transducer mounted in said hollow chamber which is capable of sending and receiving sound through said annular rim, and a solid, resilient tire member mounted on the annular rim on the side thereof opposite said hollow chamber, the hollow chamber in each said wheel probe and the duct means in said wheel probe support means being filled with acoustic coupling liquid such that said obturator will act to balance the pressure of said acoustic coupling liquid in said inspection device with the pressure of the ambient environment.

6. The inspection device of claim 5 wherein each said obturator comprises a resilient diaphragm.

7. The inspection device of claim 5 wherein said wheel probe support means mounts two said wheel probes, the hollow chamber of each wheel probe being filled with acoustic coupling liquid which is in fluid communication with the acoustic coupling liquid in the duct means in said wheel probe support means.

8. The inspection device of claim 5 wherein the solid, resilient tire member of each wheel probe is composed of polyurethane.

9. An inspection vehicle which includes a hollow tubular member and a multiplicity of inspection devices as defined in claim 5 mounted therearound.

* * * * *